United States Patent [19]
Gilad et al.

[11] Patent Number: 5,646,188
[45] Date of Patent: Jul. 8, 1997

[54] POLYAMINE DERIVATIVES OF 1-AMINOINDAN

[75] Inventors: Gad Gilad; Varda Gilad, both of Givatayim; Jeffrey Sterling, Jerusalem; Yaacov Herzig, Raanana; David Lerner, Jerusalem; Alex Veinberg, Rehovot; Isaac Milman, Maale Adumim; Nina Finkelstein, Jerusalem, all of Israel

[73] Assignee: Teva Pharmaceutical Industries, Ltd., Jerusalem, Israel

[21] Appl. No.: 498,095

[22] Filed: Jul. 5, 1995

[51] Int. Cl.$^6$ .................. A61K 31/135; A61K 31/155; C07C 211/42; C07C 279/12
[52] U.S. Cl. .................. 514/634; 514/632; 514/657; 514/616; 564/222; 564/228; 564/236; 564/237; 564/428
[58] Field of Search .................. 564/228, 236, 564/237, 428, 222; 514/632, 634, 657, 616

[56] References Cited

U.S. PATENT DOCUMENTS

| | | | |
|---|---|---|---|
| 3,637,740 | 1/1972 | Sarges | 548/578 |
| 3,953,506 | 4/1976 | Spicer et al. | 564/428 |
| 4,792,628 | 12/1988 | Oshiro et al. | 564/428 |
| 4,876,284 | 10/1989 | Arvidsson et al. | 514/657 |
| 4,906,779 | 3/1990 | Weber et al. | 564/238 |
| 4,969,679 | 11/1990 | Junge et al. | 514/222.2 |
| 5,196,454 | 3/1993 | Grauert et al. | 514/654 |
| 5,376,687 | 12/1994 | Hacksell | 514/657 |

OTHER PUBLICATIONS

Bergeron, R.J. and McManis, J.S. (1987) J. Org. Chem. 52:1700–1703.
Drugs Fut. (1991) 16:165–167.
Gilad, G.M. and Gilad, V.H. (1989) Life Sciences 44:1963–1969.
Gilad, G.M. and Gilad, V.H. (1991) Experimental Neurology 111:349–355.

*Primary Examiner*—Richard L. Raymond
*Attorney, Agent, or Firm*—John P. White

[57] ABSTRACT

A compound of general formula I

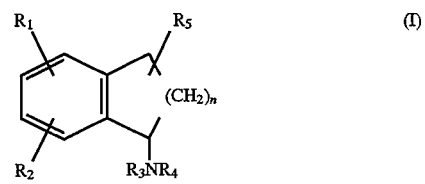

wherein n is 1 or 2;

$R_1$ and $R_2$ are each independently hydrogen, hydroxy, substituted or unsubstituted $C_{1-4}$ alkyl, substituted or unsubstituted $C_{1-4}$ alkoxy or halogeno;

$R_5$ is hydrogen, substituted or unsubstituted $C_{1-4}$ alkyl, amino or $NR_6R_7$;

$R_3$, $R_4$, $R_6$ and $R_7$ are each independently hydrogen or $(CH_2)_m$—$[NH(CH_2)_x]_y$—$NHR_{11}$ wherein m is from 0–5, y is from 0–5 and each x is independently from 1–5 and $R_{11}$ is hydrogen or $C(NH)NH_2$;

provided that when $R_3$ and $R_4$ are both hydrogen, $R_5$ is amino or $NR_6R_7$; pharmaceutically acceptable salts and optically active isomers thereof.

41 Claims, 5 Drawing Sheets

FIGURE 1A

Scheme I

FIGURE 1B

Scheme I cont.

POLYAMINE DERIVATIVES OF 1-AMINOINDAN

Throughout this application, various references are referred to. Disclosures of these publications in their entireties are hereby incorporated by reference into this application to more fully describe the state of the art to which this invention pertains.

BACKGROUND OF THE INVENTION

The present invention relates to novel polyamines, compositions containing them and their use in the treatment of neurotrauma such as stroke.

Polyamines as a class of compounds have been reported to possess a wide range of activities both within and external to the central nervous system. Such activities include modulation of postsynaptic receptors, such as nicotinic, glutamic and N-methyl-D-aspartate receptors, modulation of calcium regulatory processes as well as antiplatelet, antiinflammatory and anticoagulant activity.

Various polyamine containing molecules have been synthesized and screened in a variety of animal models of disorders of the central nervous system. Many of these compounds have been based on toxins extracted from spiders such as *A. aperta* and *Argiope labata* and the wasp *P. triangulum*. These compounds comprise a long poly(aminoalkane) chain linked to an aromatic or heterocyclic group through a carbonyl group.

Guanidine derivatives of polyamines, e.g. SFTX-33 have been reported as voltage-sensitive calcium channel blockers and EAA antagonists capable of binding at the PCP site on the NMDA receptor. U.S. Pat. No. 4,906,779 (Oregon 1990). Spergualine and deoxypergualine has been reported (R. J. Bergeron, J. S. McManis, *J. Org. Chem.*, 52, 1700 (1987); *Drug Fut.*, 16, 165 (1991)) to possess immunosuppressant activity and beneficial effect in the treatment of Multiple Sclerosis.

sFTX-33 spergualine (R = OH)
deoxyspergualine (R = H)

Gilad G et al. (Life Sci. (1989) 44 1963–1969 and Exp. Neurol. (1991) 111 349–355) have described activity of the polyamines spermine, spermidine and putrescine in protecting against ischemia induced nerve cell death in gerbils.

Disadvantages associated with using the simple polyamines described in Gilad G et al. relate to transport through biological membranes and various toxic side effects that would hinder these compounds from proceeding to clinical use.

Accordingly, the present invention provides derivatives of spermine, spermidine, and putrescine and guanidine derivatives thereof that retain the activity of the polyamine but display fewer undesirable side effects.

SUMMARY OF THE INVENTION

This invention provides compounds of general formula I wherein n is 1 or 2;

$R_1$ and $R_2$ are each independently hydrogen, hydroxy, substituted or unsubstituted $C_{1-4}$ alkyl, substituted or unsubstituted $C_{1-4}$ alkoxy or halogeno;

$R_5$ is hydrogen, substituted or unsubstituted $C_{1-4}$ alkyl, amino or $NR_6R_7$;

$R_3$, $R_4$, $R_6$ and $R_7$ are each independently hydrogen or $(CH_2)_m$—$[NH(CH_2)_x]_y$—$NHR_{11}$ wherein m is from 0–5, y is from 0–5 and each x is independently from 1–5, $R_{11}$ is hydrogen or $C(NH)NH_2$:

provided that when $R_3$ and $R_4$ are both hydrogen, $R_5$ is amino or $NR_6R_7$; pharmaceutically acceptable salts and optically active isomers thereof.

DETAILED DESCRIPTION OF THE INVENTION

This invention provides compounds of general formula I wherein n is 1 or 2;

$R_1$ and $R_2$ are each independently hydrogen, hydroxy, substituted or unsubstituted $C_{1-4}$ alkyl, substituted or unsubstituted $C_{1-4}$ alkoxy or halogeno;

$R_5$ is hydrogen, substituted or unsubstituted $C_{1-4}$ alkyl, amino or $NR_6R_7$;

$R_3$, $R_4$, $R_6$ and $R_7$ are each independently hydrogen or $(CH_2)_m$—$[NH(CH_2)_x]_y$—$NHR_{11}$ wherein m is from 0–5, y is from 0–5 and each x is independently from 1–5, $R_{11}$ is hydrogen or $C(NH)NH_2$;

provided that when $R_3$ and $R_4$ are both hydrogen, $R_5$ is amino or $NR_6R_7$; pharmaceutically acceptable salts and optically active isomers thereof.

Within general formula I it is generally preferred that n is 1, that is the compounds are derivatives of 1-aminoindan. It is further preferred that $R_1$ and $R_2$ are each independently hydrogen, hydroxy or halogeno, most preferably $R_1$ and $R_2$ are both hydrogen. In a more specific embodiment $R_1$, $R_2$ and $R_5$ are hydrogen.

In one embodiment of the invention one of $R_3$ and $R_4$ is hydrogen and the other is of the formula $(CH_2)_m$—$[NH(CH_2)_x]_y$—$NHR_{11}$. In such an embodiment it is preferable that $R_{11}$ is hydrogen, m is 3 or 4, y is 0,1 or 2 and x where appropriate is 3 or 4. When y is more than 1 it is preferable that each x is 3 or 4.

Alternatively, one of $R_3$ and $R_4$ are hydrogen and the other is of the formula $(CH_2)_m$—$[NH(CH_2)_x]_y$—$NH$—$C(NH)NH_2$, i.e. $R_{11}$ is $C(NH)NH_2$, m, y and x being as defined above.

In an alternative embodiment both R3 and $R_4$ are of the formula $(CH_2)_m$—$[NH(CH_2)_x]_y$—$NHR_{11}$. In this alternative embodiment it is preferable that m is 3 or 4 and y is 0, 1 or 2 more preferably 0. In a specific embodiment, $R_{11}$ is H.

In a further alternative embodiment of the invention, both $R_3$ and $R_4$ are hydrogen and $R_5$ is amino or $NR_6R_7$, wherein $R_6$ and $R_7$ are each independently hydrogen or of the formula $(CH_2)_m$—$[NH(CH_2)_x]_y$—$NHR_{11}$ with m, x, y and $R_{11}$ taking the preferences described above. Preferably $R_5$ is amino or $N(CH_2)_m$—$[NH(CH_2)_x]_y$—$NHR_{11}$ with m being 3 or 4, y being 0 and $R_{11}$, hydrogen.

The compounds of formula I are aminoindan or aminotetralin analogs of spermine, spermidine, and putrescine and guanidine derivatives thereof and isomers of these polyamines. Many of the compounds of general formula I are optically active. The present invention further relates to the purified optically active isomers.

In such embodiments when $R_5$ is not hydrogen, the $R_5$ group may exist in either the cis or trans configuration with respect to the group $NR_3R_4$. In such circumstances it is preferable that $R_5$ and the group $NR_3R_4$ are in the cis configuration.

In all the above embodiments, the ring carbon to which the $NR_3R_4$ group is bound may be in the "R" or "S" configuration, preferably it is in the "R" configuration.

Specific embodiments of the compound of general formula I include the following:

N-(3-aminopropyl)-1-aminoindan;
N-(4-aminopropyl)-1-aminoindan;
N,N-di(4-amino-n-butyl)-1-aminoindan;
(R)-N,N-di(4-amino-n-butyl)-t-aminoindan;
(S)-N,N-di(4-amino-n-butyl)-1-aminoindan;
N-(4-amino-n-butyl)-N-(3-amino-n-propyl)-1- aminoindan;
N,N-di(4-amino-n-butyl)-1-amino-1, 2, 3, 4-tetrahydronaphthalene;
N-[N-(4-aminobutyl)-3-aminopropyl)]-1-aminoindan;
N-[N-(3-aminopropyl)-4-aminobutyl)]-1-aminoindan;
N-{[N-(3-aminopropyl)-4-aminobutyl)]-N'-3-aminopropyl}-1-aminoindan;
N-{[N-(4-aminobutyl)-3-aminopropyl)]-N'-4-aminobutyl}-1-aminoindan;
cis N,N'-diacetyl-1,3-diaminoindan;
trans N,N'-diacetyl-1,3-diaminoindan;
cis 1,3-diaminoindan;
trans 1,3-diaminoindan;
N-(4-aminobutyl)-1,3-diaminoindan;
N,N'-di(4-aminobutyl)-1,3-diaminoindan;
N-(3-aminopropyl)-N-[N-(3-aminopropyl)-4-aminobutyl]-1-aminoindan;
N,N-di(4-guanidinobutyl)-1-aminoindan;
N-(4-guanidinobutyl)-1-aminoindan, and pharmaceutically acceptable salts thereof.

The present invention also provides a pharmaceutical composition comprising a therapeutically effective amount of at least one of the above-listed compounds and a pharmaceutically acceptable carrier.

This invention provides for the pharmaceutical composition wherein the pharmaceutically acceptable carrier is a solid and the pharmaceutical composition is a tablet. In an embodiment the therapeutically effective amount is from about 1 mg to about 1000 mg. In a more specific embodiment the therapeutically effective amount is from about 10 mg to about 100 mg.

In another embodiment of the pharmaceutical composition the pharmaceutically acceptable carrier is a liquid and the pharmaceutical composition is an injectable solution. In a specific embodiment the therapeutically effective amount is from about 1 mg/ml to about 1000 mg/ml. In a more specific embodiment the therapeutically effective amount is from about 10 mg/ml to about 100 mg/ml.

In an embodiment of the pharmaceutical composition the carrier is a gel and the pharmaceutical composition is a suppository.

This invention further provides a method for treating acute neurological traumatic disorder or neurotrauma in a subject comprising administering to the subject a therapeutically effective amount of a compound of the formula I or pharmaceutically acceptable salt thereof, effective to treat the acute neurological traumatic disorder or neurotrauma on the subject.

The subject can be any vertebrate, but is preferably a mammal, for example a cow, goat, sheep, horse, dog, monkey, ape, rabbit, rat or mouse. Most preferably the mammalian subject is a human.

The subject invention further provides a method of treating a subject afflicted with a neurodegenerative disease which comprises administering to the subject an amount of a compound of general formula I or the pharmaceutically acceptable salt thereof of the subject invention effective to treat the neurodegenerative disease in the subject.

The subject invention further provides a method of treating a subject afflicted with a neurotoxic injury which comprises administering to the subject an amount of a compound of general formula I or the pharmaceutically acceptable salt thereof of the subject invention effective to treat the neurotoxic injury in the subject.

The subject invention further provides a method of treating a subject afflicted with brain ischemia which comprises administering to the subject an amount of a compound of general formula I or the pharmaceutically acceptable salt thereef of the subject invention effective to treat brain ischemia in the subject.

The subject invention further provides a method of treating a subject afflicted with a head trauma injury which comprises administering to the subject an amount of a compound of general formula I or the pharmaceutically acceptable salt thereof of the subject invention effective to treat the head trauma injury in the subject.

The subject invention further provides a method of treating a subject afflicted with a spinal trauma injury which comprises administering to the subject an amount of a compound of general formula I or the pharmaceutically acceptable salt thereof of the subject invention effective to treat the spinal trauma injury in the subject.

The subject invention further provides a method of preventing nerve damage in a subject which comprises administering to the subject an amount of general formula I or the pharmaceutically acceptable salt thereof of the subject invention effective to prevent nerve damage in the subject.

The terms acute neurological traumatic disorder or neurotrauma are used herein to refer to, and include clinical indications such as strokes, acute cranial injury.

The compounds of the present invention are also of use as immunosuppressants, as anti-neoplastic agents, anti-psoratic agents and in the treatment of epilepsy, Alzheimer's Disease, multiple sclerosis, as insecticides and pesticides against endo- and ectoparasites.

The compound of general formula I, its salts and optically active isomers can be administered using techniques well known in the art. For example, the compound may be administered orally, rectally, parenterally, intravenously, or intramuscularly.

To aid the discussion of the preparation of the compounds of the present invention it is convenient to classify them as follows:

1) Diamines (e.g. derivatives of putrescine or analogues with a different number of methylene groups in the alkyl chain;
2) Triamines (e.g. derivatives of spermidine or analogues with differing numbers of methylene groups in the alkyl chain;
3) Tetramines (e.g. derivatives of spermine or analogues with differing numbers of methylene groups in the alkyl chain;
4) Compounds with five or more amino groups which are not direct derivatives of natural polyamines.

Figure 1A:
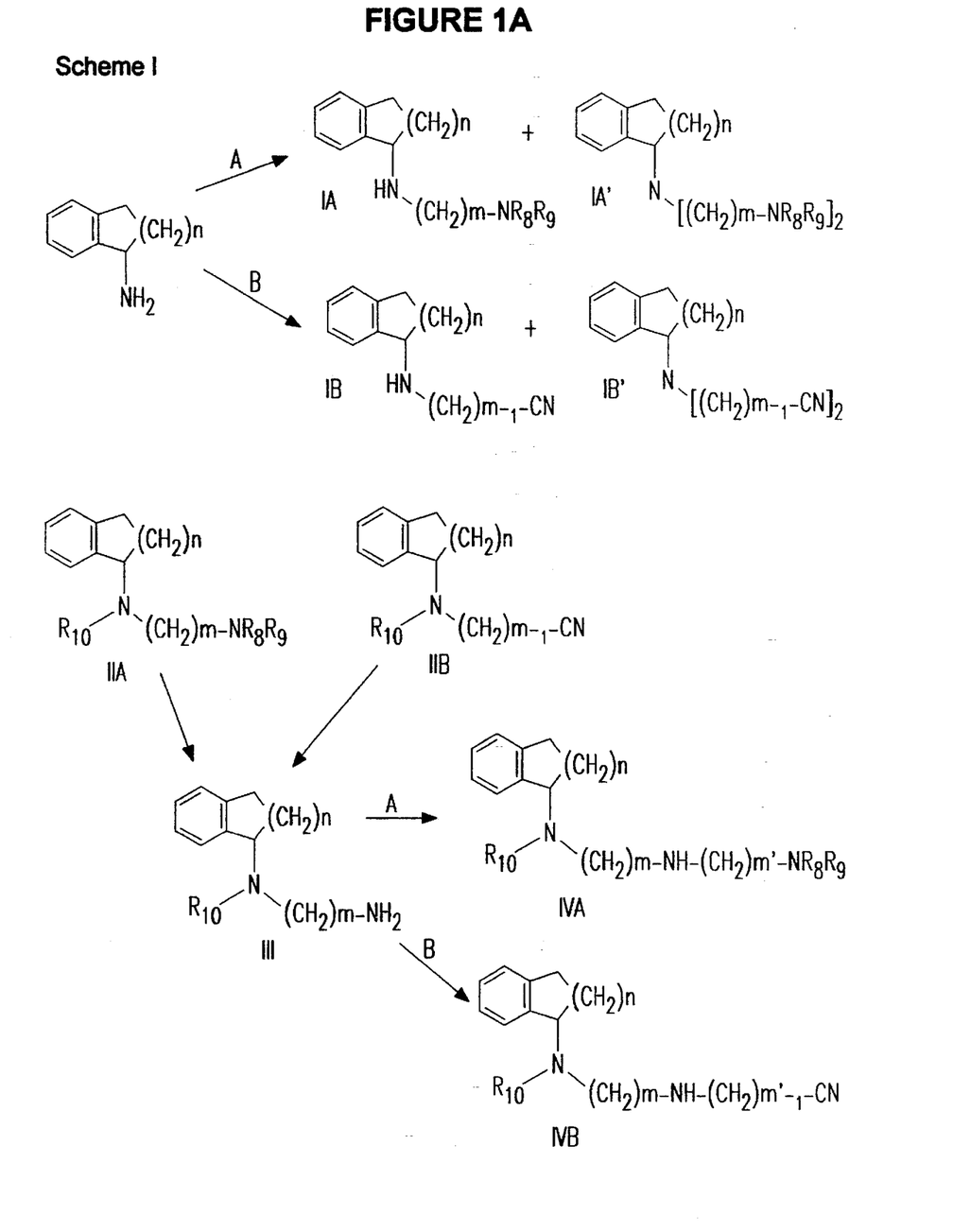
FIG. 1A: Scheme I—Schematic of chemical synthesis Examples 1–5.
Figure 1B:
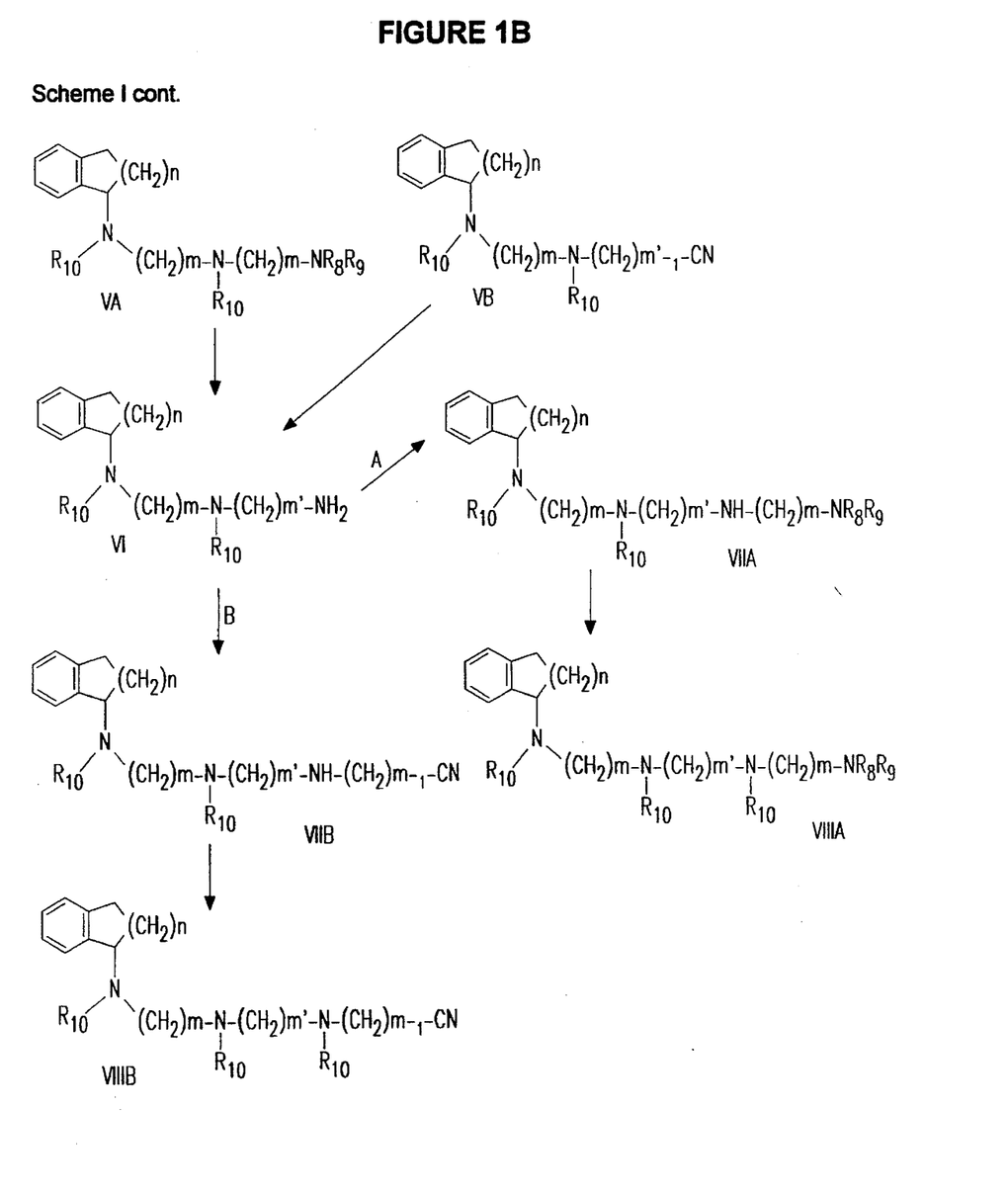
FIG 1B: Scheme I continued.
Figure 2:
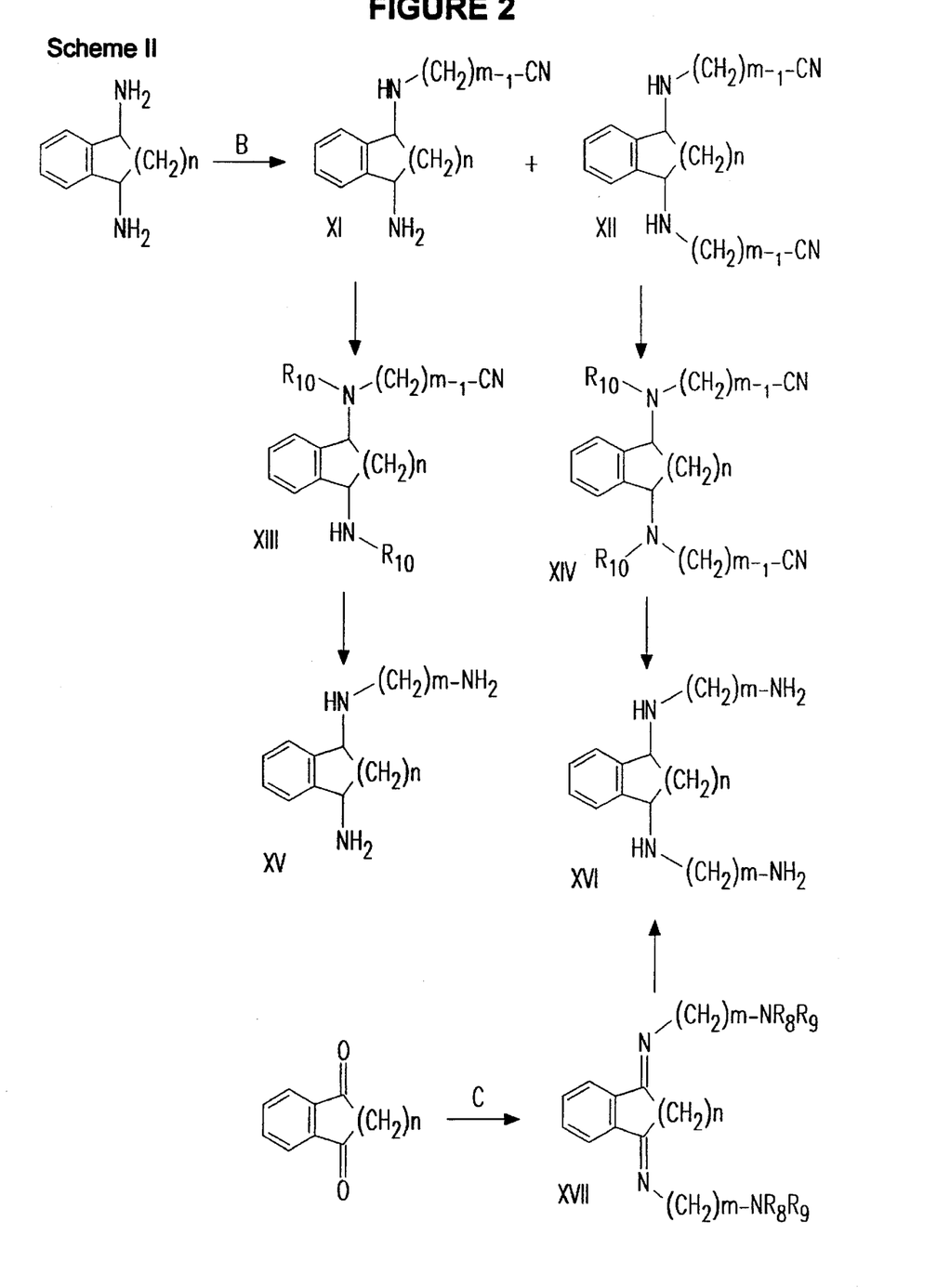
FIG. 2: Scheme II—Schematic of chemical synthesis Example 6.

With reference to the schemes diagrammed in FIGS. 1 and 2, the compounds of the present invention may be prepared from the parent 1-aminoindan or 1-aminotetralin by reaction with a compound of the formula A or B.

A

B wherein m is defined as previously and X is a suitable leaving group (such as halide or sulfonate ester) to enable N-alkylation by A or B; and one or both of $R_8$ and $R_9$ are suitable amino protecting groups such as t-butyloxycarboxy (BOC) or together are phthaloyl. Alternatively the terminal nitrile group of compound B fulfills the same role as an amine protecting group.

The reaction between the 1-aminoindan or 1-aminotetralin can be controlled to give predominantly either diamines or symmetrical triamines or a mixture of the two which may be separated into pure compounds by methods known to those skilled in the art (chromatography, crystallization, etc.). The desired diamines or symmetrical triamines may be isolated by removing the protecting groups under the appropriate conditions. For example if Rs in IA is BOC, treatment with hydrogen chloride in ether. If $R_8R_9$ in IA is phthaloyl, treatment with hydrazine. If the protecting group is nitrile in IB it is reduced with lithium aluminum hydride (LAH). In general the diamine is isolated as the salt of a suitable acid (e.g. hydrochloric, sulfuric, methansulfonic, etc.).

Unsymmetrical triamines may be prepared by reacting a second alternative compound of the formula A or B with the partially protected diamine (I). The terminal protecting groups may then be removed according to methods described immediately above.

Other unsymmetrical triamines may be prepared by reacting a second alternative compound of the formula A or B and the suitably protected diamine (III) which is prepared from partially protected diamine (i) by introducing a second protecting group on the secondary amine to give fully protected diamine (II). The second protecting group ($R_{10}$) is chosen so that the terminal primary amine protecting group ($R_8R_9$ or nitrile) may be selectively converted to a free amine in its presence. For example, if $R_8R_9$ is phthaloyl, $R_{10}$ may be BOC. In the case where $R_8R_9$ of the fully protected diamine (IIA) is phthaloyl, it may be selectively removed by treatment with hydrazine to give a compound of formula (III). In the case where the fully protected diamine (IIB) has a nitrile group, it may be selectively reduced with LAH likewise to give a compound of formula (III). In either case, the resulting compound of formula (III) may be reacted with a compound of formula A or B as described above to give a partially protected triamine of formula (IV). The desired triamine may be isolated as a suitable salt by removal of the protecting goups under the appropriate conditions as described above and subsequent reaction with a suitable acid.

Alternatively, the partially protected triamine (IV) may be converted to a tetramine by repeating the process described above (full protection to (V) and selective deprotection to (VI). The resulting partially protected tetramine (VII) may be fully deprotected to isolate the tetramine or the protection/partial deprotection may be repeated to a pentamine, or higher homologue.

In a further embodiment of the invention the indan or tetralin skeleton forms an integral part of the polyamine structure. In this case the diamine compound may be 1,3-diaminoindan (or 1,3-diaminotetralin) or 1,4-diaminotetralin. Each analogue may be isolated as the cis or trans isomer. They may be prepared from the corresponding diketone by reaction with hydroxylamine hydrochloride followed by reduction (preferably using sodium in alcohol (preferably ethanol or isopropanol) or catalytic hydrogenation, preferably with palladium on carbon. The resulting cis/trans mixture of diamines may be resolved by any convenient means, preferably by conversion to the diacetyl amide and resolution by crystallization and/or chromatography. The isomerically pure diacetates may be hydrolyzed to the desired diamines under acidic conditions (preferably aqueous hydrochloric acid).

In analogy to the procedures described above, these diamines may be converted to triamines and tetramines by reaction with compounds of the formula A or B (preferably B). In general, such a reaction results in a mixture of triamine (XI) and tetramine (XII) which may be separated by any convenient means, preferably by chromatography after converting them to the fully protected analogues (XIII) and (XIV), $R_{10}$ preferably is BOC. After resolution, the protecting groups are removed from the resulting pure compounds (XIII) and (XIV) preferably using LAH for the nitrile and hydrogen chloride in ether for the BOC. The desired compounds (XV) are thus isolated as a suitable salt (hydrochloride, sulfuric acid, methanesulfonic acid etc) as relatively pure cis or trans isomers.

In a further embodiment of the invention, tetramines of the formula XVI can alternatively be prepared directly from the indan or tetralin diketone by reaction with a monoprotected diamine of formula C or D NH$_2$—(CH$_2$)$_m$—NR$_8$R$_9$    C NH$_2$—(CH$_2$)$_{m-1}$—CN    D where m, R$_8$ and R$_9$ are all as defined previously, to give the corresponding imine (XVII) which may be reduced (preferably with sodium borohydride or by catalytic hydrogenation) followed by deprotection under conditions appropriate for the protecting group, preferably acid hydrolysis for the case where R$_8$ is BOC. In this case XVI is isolated as a mixture of cis and trans isomers.

Figure 3:
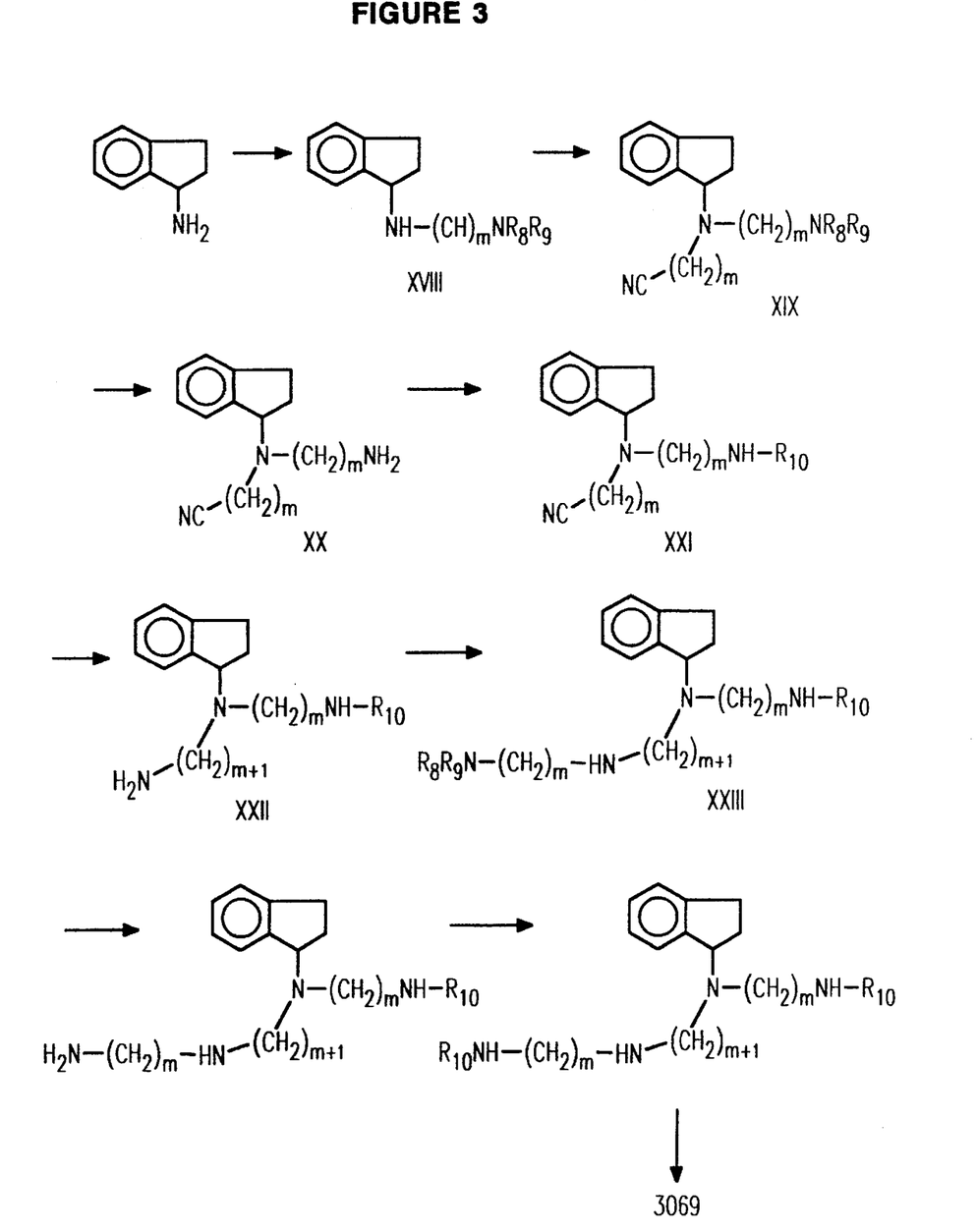
FIG. 3: Scheme III—Schematic of chemical synthesis of Example 7.

Unsymmetrical tetramines, e.g. compound 3069, may be prepared from th partially protected triamine (XXII) by introducing an appropriately protected aminoalkyl group, followed by removal of the protecting groups.

The triamine XXII may be prepared from 1-aminoindan by stepwise alkylations, starting with a protected aminoalkyl group, followed by a cyanoalkyl moiety. The nitrile group may subsequently be reduced with LAH and protected to give XXII.

Figure 4:
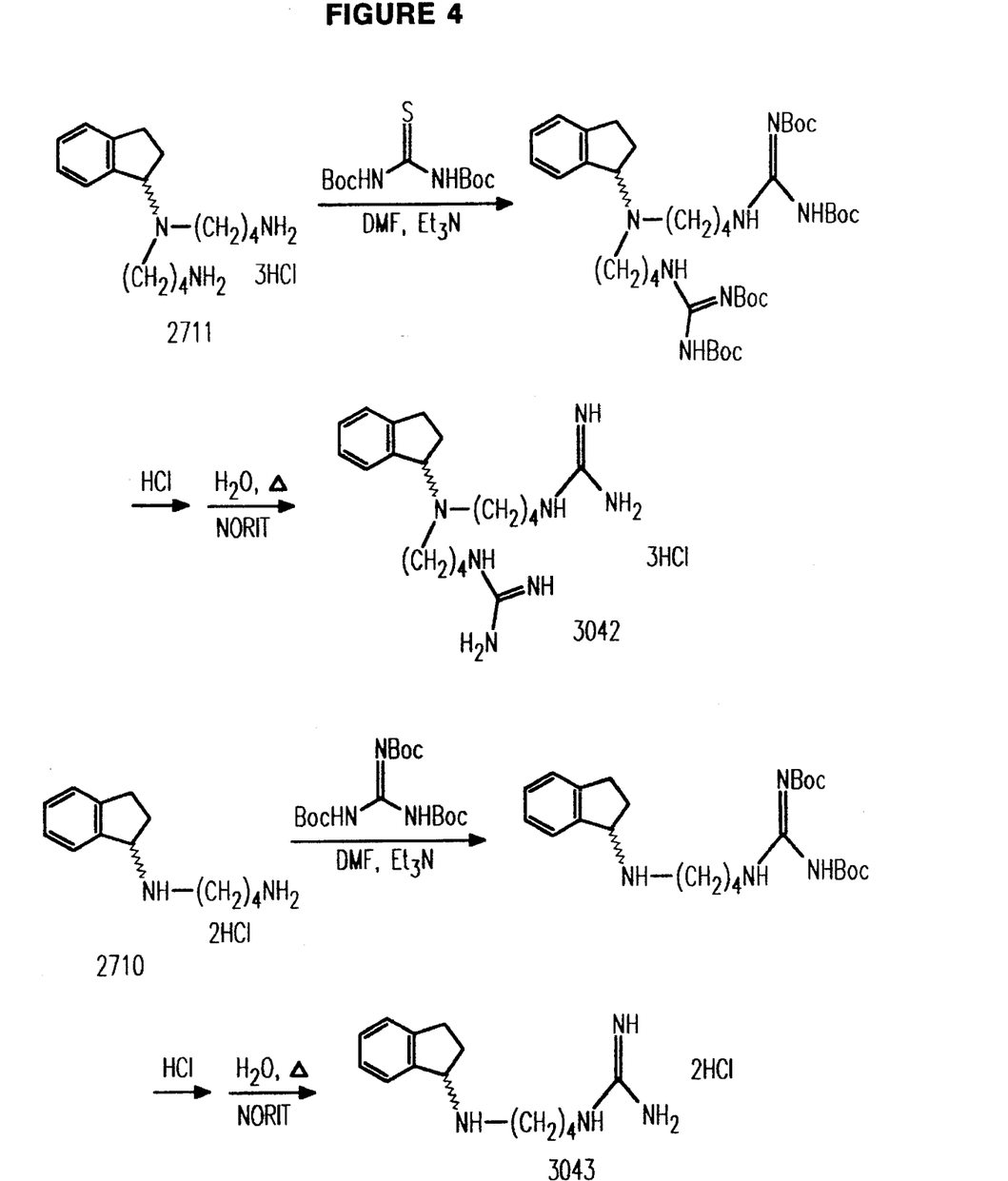
FIG. 4: Schematic of chemical synthesis of Example 8.

The guanidine derivatives (compounds 3042, 3043) may be prepared by reacting the corresponding diamines or triamines with a guanylating agent e.g. N,N-di-tert-butoxycarbonylthiourea, (Iwanowicz E et al. Synthetic Communications (1993) 23, 1443), in a polar aprotic medium e.g. DMF, in the presence of an organic base e.g. triethylamine, optionally in the presence of a metal halide e.g. copper chloride or mercuric chlorides, and finally removing the Boc protecting groups by known methods, such as gaseous HCl in organic solvents.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Many of the specific compounds are identified by a four-digit number from 2709 to 2732 and 3042, 3043 and 3069. Structures and names of these compounds may be found immediately following Chemical Synthesis Example 8.

CHEMICAL SYNTHESIS EXAMPLES

Example 1

Preparation of Phthalimidoalkylaminoindans [6]

A mixture of 0.14 mol of aminoindan or IA, 0.14 mol of bromoalkylphthalimide and 0.14 mol of K$_2$CO$_3$ in 180 ml of MeCN was stirred at bath temperature 50° C. for 8 hours. After cooling and filtration, the mother liquor was evaporated. The residue was chromatographed on Keiselgel. Eluent: hexane-ethyl acetate 1:1.

In this way the following compounds were prepared;

Compounds of the formula 1A m=3, 56% yield.

$^1$H-NMR(CDCl$_3$), delta, ppm: 7.85–7.63 (m,4H,), 7.31–7.10 (m,4H,), 4.2 (t,J=6.5Hz,1H), 3.83–3.81 (m,2H), 3.01–2.95 (m, 1H), 2.83–2.71 (m,3H), 2.40–2.33 (m, 1H), 1.94–1.56 (m, 3H).

m=4, 54% yield.

$^1$H-NMR(CDCl$_3$), delta, ppm: 7.88–7.65 (m,4H,), 7.32–7.15 (m,4H,), 4.22 (t,y=6.5Hz,1H), 3.79–3.68 (m,2H), 3.02–2.95 (m, 1H), 2.85–2.73 (m, 3H), 2.43 –2.34 (m, 1H), 1.87–1.22 (m, 5H), and Compounds of formula 1A' m=m'=4, 8% yield.

$^1$H-NMR(CDCl$_3$), delta, ppm: 7.88–7.68 (m,8H), 7.32–7.11 (m,4H) , 4.46 (t,y=7.5Hz,1H), 3.68–3.62 (m,4H) , 2.90–2.65 (m,2H), 2.48–2.33 (m,4H), 2.10–1.85 (m,2H), 1.80–1.45 (m, 8H), m=3, m'=4, 26% yield using a 100% excess of bromopropylphthalimide.

$^1$H-NMR(CDCl$_3$), delta, ppm: 7.83–7.66 (m,8H), 7.33–7.10 (m,4H), 4.50 (t,y=7.5Hz,1H), 3.86–3.65 (m,4H), 2.90–2.75 (m,2H), 2.51–2.40 (m,4H), 2.10–1.5t(m,8H), Example 2

Hydrazinolysis of phthalimidoaminoindans [1]

A mixture 3.5 mmol of phthalimidoaminoindan (as prepared in Example 1) and 60% excess of 64% N$_2$H$_4$. H$_2$O in 40 ml of abs. ethanol was refluxed winh stirring for 1.5 hrs. After cooling and filtration the mother liquor was evaporated and the substance was extracted by reflux with 50 ml of ethyl acetate. The solvent was evaporated. The residue was dissolved in 15 ml of ether and gas HCl in ether (15 ml pH<1) was added with stirring. The residue was filtered.

In this way the following compounds were prepared;

m=3 (2709) recrystallized from ethyl acetate/ethanol (1.6:1), 82% yield, mpt 153°–154° C.

$^1$H-NMR($D_2O$), delta, ppm: 7.60–7.39 (m,4H), 4.91–4.82 (m, 1H), 3.28–3.02 (m,6H), 2.67–2.58 (m, 1H), 2.34–2.26 (m, 1H), 2.17–2.10 (m, 2H). IR (KBr, disc), $cm^{-1}$ 750, 1606,1512, 3000–2500, 1444), 2700–2400, 3250. m/z 190MH$^+$ (free base) Anal. Calc. for $C_{12}H_{20}Cl_2N_2$, C 54.75%, H 7.00%, Cl 26.94%, N 10.65% Found C 55.06%, H 7.82%, Cl 26.00%, N 11.31% m=4 (2710) recrystallized from ethyl acetate/ethanol (1.6:1), 83% yield, mpt 214°–216° C. (decomp).

$^1$H-NMR($D_2O$), delta, ppm: 7.56–7.34 (m,4H), 4.86–4.81 (m, 1H), 3.21–2.98 (m,6H), 2.60–2.53 (m, 1H), 2.30–2.23 (m, 1H), 1.82–1.73 (m, 4H). m/z 205MH$^+$ (free base).
and compounds;

m=m'=4 (2711)
was prepared by dissolution in water and stirring with Norit. After filtration and evaporation of water the residue was triturated with ether and crystallized from iso-propanol-ethanol 2:1, 45% yield.

$^1$H-NMR($D_2O$) , delta, ppm: 7.55–7.37 (m,4H) , 5.24–5.21 (m, 1H), 3.20–2.89 (m,10H), 2.57–2.51 (m, 1H), 2.39–2.32 (m, 1H), 1.90–1.56 (m, 8H). IR (KBr, disc), $cm^{-1}$ 770–735, 1480–1440: 3000–2800, 1600,1500, 3000, 2500, 2000, 1600–1575 m/z 275MH$^+$ (free base) Anal. Calc. for $C_{17}H_{32}Cl_3N_3$, C 53.20%, H 8.40%, Cl 27.45%, N 10.95% Found. C 53.01%, H 8.08%, Cl 28.84%, N 11.16%.

m=m'=4 (R)-enantiomer of 2711, (2726)

The above procedure was repeated using (R)-aminoindan as the starting material and recrystallizing from ethanol-isopropanol. Yield 57%, mpt >280° C.

$^1$H-NMR($D_2O$) , delta, ppm: 7.65–7.40 (m,4H) , 5.25 (m, 1H) , 3.35–2.90 (m,10H), 2.57 (m, 1H), 2.41 (m, 1H), 2.05–1.60 (m, 8H). IR (KBr, disc) , $cm^{-1}$ 3000–2850, 2046, 2010, 1616, 1606, 1532, 1512, 1470, 1446, 1017, 974, 775, 747. m/z 276 (MH$^+$, 100, free base) Anal. Calc. for $C_{17}H_{32}Cl_3N_3$, C 53.06%, H 8.38%, Cl 27.64%, N 10.92% Found. C 52.35%, H 8.46%, N 10.85%. [alpha]$_D$=−6.0° ($H_2O$)

m=m'=4, (S)-enantiomer of 2711, (2727)

The above procedure was repeated using (S)-aminoindan as the starting material. Yield 56%, mpt >280° C. Spectral properties were identical to 7262 above. [alpha]$_D$=+6.4° ($H_2O$)

Similarly, the enantiomers of other compounds of general formula I may be made by using the corresponding enantiomeric 1-aminoindan as the starting compound.

m=3, m'=4 (2722) 45% yield was prepared by dissolution in water and stirring with Norit. After filtration and evaporation of water the residue was triturated with ether and crystallized from iso-propanol-ethanol 2:1, 45% yield, mpt 227°–228° C.

$^1$H-NMR($D_2O$), delta, ppm: 7.56–7.39 (m,4H), 5.28–5.26 (m, 1H), 3.32–2.97 (m,10H), 2.60–2.54 (m, 1H), 2.40–1.62 (m, 7H). IR (KBr, disc), V, $cm^{-1}$ 770–735, 1480–1440: 3200–2800, 1600,1500, 3000, 2500, 2000, 1600–1575. m/z 261MH$^+$ (free base) Anal. Calc. for $C_{16}H_{30}Cl_3N_3$, C 51.82%, H 8.16%, Cl 28.69%, N 11.33% Found. C 51.34%, H 7.77%, Cl 29.85%, N 11.63%.
and compounds m=m'=4 (2728)
The above procedure was repeated using 1-aminotetralin as the starting material.

$^1$H-NMR($D_2O$), delta, ppm: 7.53 (m, 1H), 7.48–7.33 (m,3H), 5.04 (t,1H), 3.50–2.65 (m,10H), 2.35 (m, 1H), 2.15–1.40 (m, 11H). IR (KBr, disc) , V, $cm^{-1}$ 5000–2850, 2014, 1616, 1600, 1534, 1457, 1408, 1012, 773, 754. m/z 290 (MH$^+$, 100, (free base) Anal. Calc. for $C_{18}H_{34}Cl_3N_3$, C 54.21%, H 8.59%, Cl 26.67%, N 10.54% Found. C 54.33%, H 8.84%, Cl 26.17%, N 10.65%.

Example 3

3A. Protection of Secondary Amines with $BOC_2O$ [1]

A solution of 16 mmol of a secondary amine of Formula IA or IB and 24 mmol of $BOC_2O$ in 50 ml of dichloromethane was stirred at R.T. for 3 hours. The reaction mixture was washed with 5% NaOH, dried, and evaporated. The residue was purified by column chromatography on Kieselgel. Eluent: hexane-ethyl acetate 2:1. Yield 85–95%.

In this manner the following compounds were prepared

Compounds of Formula II m=3 or m=4.
m=3;
$^1$H-NMR(CDCl$_3$), delta, ppm: 7.82–7.70 (m,4H), 7.14–7.05 (m,4H) , 5.73 and 5.25 (broad s 1H) , 3.65–1.28 (m,19H) .

m=4:
$^1$H-NMR(CDCl$_3$), delta, ppm: 7.81–7.70 (m,4H), 7.13–7.00 (m,4H), 5.72 and 5.25 (broad s 1H), 3.65–1.27 (m,21H).

3B. Hydrazinolysis of BOC phthalimidoaminoindans [1.]

A mixture of 50 mmol of BOC-phthalimidoaminoindan of Formula IIA and 65 mmol of 64% $N_2H_4$. $H_2O$ in 300 ml of absolute ethanol was stirred at bath temperature 50° C. for 10 hours. After cooling and filtration the mother liquor was evaporated. The residue was distributed in a mixture of ether-water. The ether phase was dried and evaporated, the residue was purified on Kieselgel. Eluent: dichloromethane-methanol-conc. ammonia 65:10:1. Yield 70–80%.

In this manner the following compounds were prepared;

Compounds of Formula III m=3;
¹H-NMR(CDCl₃), delta, ppm: 7.21–7.13 (m,4H), 5.78 and 5.27 (broad s,1H), 3.28–1.21 (m,19H).
m=4:
¹H-NMR(CDCl₃), delta, ppm: 7.20–7.14 (m,4H), 5.77 and 5.27 (broad s,1H), 3.19–1.20 (m,21H).

3C. Alkylation of Primary Amines

A mixture of 41.4 mmol of a primary amine of Formula III, 82.8 mmol of Cl(CH₂)$_{m'-1}$CN and 124 mmol of K₂CO₃ in 120 ml of acetonitrile was refluxed with stirring for 3 hours, then an additional 41.4 mmol of Cl(CH₂)$_{m'-1}$CN was added, and the mixture was refluxed for 4 hours. After addition of a further 82.8 mmol of Cl(CH₂)$_{m'-1}$CN the reaction mixture was refluxed for 3 hours. After cooling, filtration and evaporation, the residue was purified by column chromatography on Kieselgel. Eluent: dichloromethane-methanol 95:5. Yield 60–65%. m is 3 or 4 depending on the compound being synthesized.

In this manner the following compounds were prepared;

Compounds of Formula IV m=3, m'=4
¹H-NMR(CDCl₃), delta, ppm: 7.21–7.15 (m,4H), 5.70 and 5.30 (broad s,1H), 2.98–1.25 (m,25H). m/z 258MH⁺

3D. Protection of Secondary Amines with BOC₂O

A solution of 16 mmol of a secondary amine of Formula IVA or IVB and 24 mmol of BOC₂O in 50ml of dichloromethane was stirred at R.T. for 3 hours. The reaction mixture was washed with 5% NaOH, dried, and evaporated. The residue was purified by column chromatography on Kieselgel. Eluent: hexane-ethyl acetate 2:1. Yield 85–95%.

In this manner the following compounds were prepared;

Compounds of Formula V m=3, m'=4
¹H-NMR(CDCl₃), delta, ppm: 7.21–7.16 (m,4H), 5.78 and 5.28 (broad s,1H), 3.10–1.24 (m,34H).

3E. Reduction of Nitriles with LiAlH₄

To a suspension 4.0 g of LiAlH₄ in 150 ml of ether 5.8 mmol a nitrile of Formula VB in 50 ml of ether was added with stirring in an ice-bath, the suspension was then stirred without ice-bath for 0.5 hrs. Excess of LiAlH₄ was destroyed followed by addition of 4.0 ml of water, 4.0 ml of 10% NaOH and 12.0 ml of water with cooling. The organic phase was decanted and additional amount of the substance was extracted by dichloromethane. The combined organic phases were washed, dried and evaporated. The residue was purified by column chromatography on Kieselgel. Eluent: dichloromethane-methanol—conc. ammonia 65:10:1. Yield 60–70%.

In this manner the following compounds were prepared;

Compounds of Formula VI m=3,m'=4
¹H-NMR(CDCl₃), delta, ppm: 7.22–7.14 (m,4H), 5.78 and 5.30 (broad s,1H), 3.04–1.26 (m,36H).

3F. Deprotection of N-BOC Derivatives

An excess of HCl in ether (18 ml, pH<1) was added to a solution 2.5 mmol of an N-BOC derivative of Formula VI in 6 ml of methanol. The mixture was stirred at R.T. for 4 hours. The precipitate was collected by filtration and washed with ether.

In this manner the following compounds were prepared;

m=3,m'=4 yield 50% mpt 239°–240° C. (2720).
¹H-NMR(D₂O), delta, ppm: 7.56, 7.34(m, 4H), 4.87–4.83 (m, 1H), 3.23–2.98 m,10H), 2.63–2.53 (m, 1H), 2.30–2.22 (m, 1H), 2.15–2.08 (m, 2H), 1.82–1.71 (m, 4H). IR (KBr, disc), cm⁻¹ 770–735, 1600, 1500, 2000, 2300–2700, 2500, 3000, 3400, 3500. m/z 262 (MH⁺, 100, free base) Anal. Calc. for C₁₆H₃₀Cl₃N₃ 0.7H₂O*, C 50.12%, H 8.18%, Cl 27.74%, N 10.96% Found. C 50.16%, H 7.98%, Cl 28.09%, N 11.17%.
m=4,m'=3 (2724) 45% yield, mpt 237°–238° C.
¹H-NMR(D₂O), delta, ppm: 7.67–7.40 (m,4H), 4.90–4.86 (m, 1H), 3.21–3.01 (m, 10H), 2.71–2.56 (m, 1H), 2.33 –2.25 (m, 1H), 2.17–2.09 (m, 2H), 1.82–1.34 (m, 4H). IR (KBr, disc), cm⁻¹ 750, 1608,1500, 2700–2250, 2943, 2500, 2042 m/z 262MH⁺ (free base) Anal. Calc. for C₁₆H₃₀Cl₃N₃ 0.7H₂O* C 50.12%, H 8.18%, Cl 27.74%, N 10.96%, Found C 49.10% H 7.81%, Cl 27.68% N 11.20%. * water content determined by Karl Fischer analysis.

Example 4

4A. Alkylation of Primary Amines

A mixture of 41.4 mmol of a primary amine of Formula VI, 82.8 mmol of Cl(CH₂)$_{m'-1}$CN and 124 mmol of K₂CO₃ in 120 ml of acetonitrile was refluxed with stirring for 3 hours, then an additional 41.4 mmol of Cl(CH$_2$)$_{m-1}$CN was added, and the mixture was refluxed for 4 hours. After addition of a further 82.8 mmol of Cl(CH$_2$)$_n$CN the reaction mixture was refluxed for 3 hours. After cooling, filtration and evaporation the residue was purified by column chromatography on Kieselgel. Eluent: dichloromethane-methanol 95:5. Yield 60–65%. m is 3 or 4 depending on the compound being synthesized.

In this manner the following compounds were prepared;

Compounds of Formula VII

BOC—N(indane)—(CH$_2$)$_m$—N—(CH$_2$)$_{m'}$—N—(CH$_2$)$_{m-1}$—CN
                         |                    |
                         BOC                  H

4B. Protection of Secondary Amines with BOC$_2$O

[1]

A solution of 16 mmol of a secondary amine of Formula VIIA or VIIB and 24 mmol of BOC$_2$O in 50 ml of dichloromethane was stirred at R.T. for 3 hours. The reaction mixture was washed with 5% NaOH, dried, and evaporated. The residue was purified by column chromatography on Kieselgel. Eluent: hexane-ethyl acetate 2:1. Yield 85–95%.

In this manner the following compounds were prepared;

Compounds of Formula VIII

BOC—N(indane)—(CH$_2$)$_m$—N—(CH$_2$)$_{m'}$—N—(CH$_2$)$_{m-1}$—CN
                         |                    |
                         BOC                  BOC

4C. Reduction of Nitriles with LiAlH$_4$

To a suspension 4.0 g of LiAlH$_4$ in 150 ml of ether 5.8 mmol a nitrile of Formula VIIIB in 50 ml of ether was added with stirring in an ice-bath, the suspension was then stirred without ice-bath for 0.5 hrs. Excess of LiAlH$_4$ was destroyed followed by addition of 4.0 ml of water, 4.0 ml of 10% NaOH and 12.0 ml of water with cooling. The organic phase was decanted and additional amount of the substance was extracted by dichloromethane. The combined organic phases were washed, dried and evaporated. The residue was purified by column chromatography on Kieselgel. Eluent: dichloromethane-methanol–conc. ammonia 65:10:1. Yield 60–70%

In this manner the following compounds were prepared;

Compounds of Formula VIII

BOC—N(indane)—(CH$_2$)$_m$—N—(CH$_2$)$_{m'}$—N—(CH$_2$)$_m$—NH$_2$
                         |                    |
                         BOC                  BOC

4D. Deprotection of N-BOC Derivatives

An excess of HCl in ether (18 ml, pH<1) was added to a solution 2.5 mmol of an N-BOC derivative of Formula VIII in 6 ml of ether. The mixture was stirred at R.T. for 4 hours. The precipitate was collected by filtration and washed with ether. The salt was stirred in water with Norit. After filtration and evaporation the residue was triturated with methanol, filtered and washed with ether.

In this manner the following compounds were prepared;

HN(indane)—(CH$_2$)$_m$—N—(CH$_2$)$_{m'}$—N—(CH$_2$)$_m$—NH$_2$.(HCl)$_4$
                       |                    |
                       H                    H m=3,m'=4 (2721) mpt >280° C.
$^1$H-NMR(D$_2$O), delta, ppm: 7.56–7.35 (m,4H), 4.88–4.85 (m, 1H), 3.24–2.98 (m,14H), 2.63–2.54 (m, 1H), 2.30–2.33 (m, 1H), 2.16–2.06 (m, 4H), 1.79–1.77 (m, 4H). m/z 319319MH$^+$ m=4,m'=3 (2725) mpt >280° C. $^1$H-NMR(D$_2$O), delta, ppm 7.56–7.34 (m,4H), 4.86–4.83 (m, mH), 3.21–3.02 (m,14H), 2.61–2.53 (m, 1H), 2.30–2.22 (m,1H), 2.16–2.19 (m, 2H) , 1.81–1.73 (m, 8H). IR (KBr, disc) , cm$^{-1}$ 750, 1610, 1500, 2700–2250(N$^+$HR), 3000, 2500, 2000 (NH$_3^+$) m/z 333MH$^+$ (free base) Anal. Calc. for C$_{20}$H$_{40}$Cl$_4$N$_4$ 0.5H$_2$O* C 49.20%, H 8.20%, Cl 29.10%, N 11.50%, Found. C 47.82%, H 8.39%, Cl29.52%, N 11.99%. * water content determined by Karl Fischer analysis.

Example 5

A. 1,3-Indandione Dioxime

A mixture of 75 g of potassium carbonate, 30 g of hydroxylamine hydrochloride, 15 g of 1,3-indandione and 300 mL of 95% ethanol was heated to reflux with stirring for 15 min at which time it was poured into 400 mL of ice. The resulting precipitate was collected by filtration, washed with cold water and dried in vacuo to give 17.9 g of the title compound as an amorphous solid. NMR (CDCl$_3$, CD$_3$OD): 7.42–7.76 (m, 4H); 3.36 (s, 2H).

B. 1,3 Diaminoindan (cis/trans)

To a solution of 20 g of a 1,3-indandione dioxime in 2 L of absolute ethanol was cautiously added 160 g of sodium in portions during 1 hr (at such a rate to maintain reflux). After disappearance of the sodium, 300 mL of water was slowly added and the solution concentrated in vacuo to remove most of the ethanol. The resulting solution was acidified with conc. hydrochloric acid to pH 1–2 followed by extraction with methylene chloride to recover unreacted started material. The aqueous layer was basified with 10% sodium hydroxide to pH 12 and extracted with methylene chloride which gave 11.7 grams of crude 1,3-diaminoindan upon solvent removal in vacuo. Purification of this material by flash column chromatography eluting with 95% ethanol/ ammonium hydroxide (400:16) gave 8.75 g of the title compound as an approximately 60/40 mixture of cis to trans isomers.

C. cis-N,N'-Diacetyl-1,3-diaminoindan (2717)

To a solution of 17.55 g of cis/trans-1,3-diaminoindan in 102 mL of pyridine was slowly added 102 mL of acetic anhydride. After 17 hrs the reaction mixture was added to 250 mL of water and 300 mL of methylene chloride. The insoluble precipitate was isolated from this three-phase mixture by filtration and dried to give 8.7 g of crude title compound which was recrystallized from ethanol to give 5.4 g pure material.

$^1$NMR (CDCl$_3$, CD$_3$OD) delta: 7.3 (s, 4H); 5.3 (m, 2H); 2.0 (s, 6H); 2.9 and 1.7 (m, 2H).

D. trans-N,N'-Diacetyl-1,3-daiminoindan (2718)

The combined methylene chloride extracts from the above example were concentrated in vacuo, suspended in 100 mL of water and basified with 10% sodium hydroxide to pH 12. Evaporation of the repeated methylene chloride extracts gave 9.4 g of crude N,N'-diacetyl-1,3-diaminoindan as a 35:65 cis/trans mixture. The title compound (3.5 g) was isolated by flash column chromatography eluting with ethyl acetate/ethanol (95:5).

$^1$NMR (CDCl$_3$, CD$_3$OD) delta: 7.35 (m, 4H); 5.59 (m, 2H); 2.33 (t, 2H); 2.02 (s, 6H).

E. cis-1,3-Diaminoindan Hydrochloride (2715)

A solution of 100 mg of cis-N,N'-diacetyl-1,3-diaminoindan in 4 mL of 5% hydrochloric acid was heated at reflux for 6 hrs at which time it was cooled and 10% sodium hydroxide was added to pH 12–13. The combined methylene chloride extracts were evaporated to dryness to give 65 mg of crude diamine which was treated with methylene chloride and etheric hydrogen chloride to give the title compound (35 mg).

$^1$NMR (CD$_3$OD) delta:7.48 (m, 4H); 4.58 (d, d, 2H); 1.74, 3.05 (m, 2H).

F. trans-1,3-Diaminoindan Hydrochloride (2716)

The title compound was prepared according to the method of the above example 5E, except that trans-N,N'-diacetyl-1,3-aminoindan was used as starting material.

$^1$NMR (CD$_3$OD) delta: 7.35 (m, 4H); 4.55 (t, 2H), 2.15 (t, 2H).

Example 6

6A. Alkylation of 1,3-Diaminoindan Dihydrochloride

A mixture 14.9 mmol of 1.3-diaminoindan dihydrochloride, 42.0mmol of 4-chlorobutyronitrile and 84.0mmol of K$_2$CO$_3$ in 50ml of acetonitrile was refluxed for 3 hrs. Then an additional 84.0mmol of 4-chlorobutyronitrile was added, and the mixture was refluxed for 4 hrs. After cooling and filtration the mother liquor was evaporated. The residue and 42.0 mmol of BOC$_2$O were dissolved in 150 ml of dichloromethane and stirred at R.T. overnight. The reaction mixture was washed with 5% NaOH, dried, and evaporated. The residue was purified by column chromatography on Kieselgel, eluting with hexane-ethyl acetate (2:1) to isolate the BOC-mono-alkylated (XIII) and di-alkylated (XIV) products.

In this manner the following compounds were prepared;

Compounds of Formulae XIII and XIV cis R=BOC, R'=CH$_2$CH$_2$CH$_2$CN, R"=H: IR (neat): 2245cm$^{-1}$ cis R=BOC, R'=R"=CH$_2$CH$_2$CH$_2$CN: IR (neat): 2245cm$^{-1}$ trans R=BOC, R"=R"=CH$_2$CH$_2$CH$_2$CN: IR (neat): 2245cm$^{-1}$ 6B. Reduction of nitriles with LiAlH$_4$ To a suspension 4.0 g of LiAlH$_4$ in 150 ml of ether 5.8 mmol a nitrile of Formula XIII or XIV in 50 ml of ether was added with stirring in an ice-bath, the suspension was then stirred without ice-bath for 0.5 hrs. Excess LiAlH$_4$ was destroyed followed by addition of 4.0 ml of water, 4.0 ml of 10% NaOH and 12.0 ml of water with cooling. The organic phase was decanted and an additional amount of the substance was extracted by dichloromethane. The combined organic phase was washed, dried and evaporated. The residue was purified by column chromatography on Kieselgel. Eluent: dichloromethane-methanol—conc. ammonia 65:10:1.

In this manner the following compounds were prepared;

cis R=BOC, R'=CH$_2$CH$_2$CH$_2$CH$_2$NH$_2$, R"=H: CiS R=BOC, R'=R"=CH$_2$CH$_2$CH$_2$CH$_2$NH$_2$: m/z 491MH$^+$ trans R=BOC, R'=R"=CH$_2$CH$_2$CH$_2$CH$_2$NH$_2$:

6C. cis-N-(4-aminobutyl)-1,3-diaminoindan trihydrochloride (2731):

A solution of the above di-BOC derivative in methanol/ether was treated with gaseous hydrogen chloride for 6 hrs at RT. The precipitate was isolated by filtration and washed with ether. A solution of this crude title compound (0.22 g) in 15 ml of methylene chloride/water (2:1) was again treated with BOC anhydride (0.62 g) and 0.28 g of potassium carbonate at 50° C. for 20 min. The organic phase was separated, washed with 5% sodium hydroxide and evaporated to dryness. Flash column chromatography on silica eluting with hexane/ethyl acetate (2:1) gave 170 mg of the tri-BOC derivative. Acidolysis was accomplished with 1 ml of trifluoroacetic acid at RT during 20 min. After evaporation of the trifluoroacetic acid, the title compound (41 mg) was isolated from methanol/ether after treatment with hydrogen chloride gas.

$^1$H-NMR (CDCl$_3$), delta, ppm: 7.85–7.80 (m, 1H), 7.68–7.56 (m,3H), 4.97–4.89 (m,2H), 3.30–3.18 (m,3H), 3.03–2.98 (m,2H), 2.43–2.37 (m, 1H), 1.98–1.77 (m,4H). m/z 220MH$^+$ (free base)

6D. trans-N,N'-(Bis-4-aminobutyl)-1,3-diaminoindan tetrahydrochloride (2732):

A solution of the above di-BOC derivative in methylene chloride was treated with BOC-anhydride at RT for 3hrs at which time the reaction mixture was washed with 5% sodium hydroxide and concentrated to dryness. The residue was purified by flash column chromatography on silica eluting with hexane/ethyl acetate (2:1) to give the tetra-BOC derivative. Acidolysis was accomplished with 1 ml of trifluoroacetic acid at RT during 20 min. After evaporation of the trifluoroacetic acid, the title compound was isolated from methanol/ether after treatment with hydrogen chloride gas.

$^1$H-NMR(CDCl$_3$), delta, ppm: 7.90–7.87 (m,2H), 7.62–7.59 (m,2H), 5.23–5.20 (m,2H), 3.30–3.15 (m,4H), 3.02–2.98 (m, 4H), 2.91–2.88 (m, 2H), 1.96–1.76 (m, 8H). m/z 291MH$^+$

Example 7:

Preparation of (XVIII)

A mixture of racemic aminoindan (12.38 g, 0.093 mol), potassium carbonate (12.84 g, 0.093 mol), N-(3-Bromopropyl)-phthalimide (24.92 g, 0.093 mol) and acetonitrile (120mL) was stirred and heated at 50°–55° C. under nitrogen for 10 hours. The mixture was then cooled and filtered under vacuum. The mother liquor was evaporated at reduced pressure to give 30.4 g of crude product which was purified by flash chromatography to give 21.27 g (71.5% yield) of an off-white solid.

Preparation of (XIX)

A mixture of XVIII (17.45 g, 0.055 mol), 4-bromobutyronitrile (8.1 g, 0.055 mol), potassium carbonate (30.19 g, 0.218 mol) and acetonitrile (440 mL) was stirred and heated at reflux under nitrogen for 5 hours. The mixture was cooled to 60° C. and additional 4-bromobutyronitrile (32.43 g, 0.219 mol) was added. The mixture was now stirred and heated at reflux under nitrogen for 20 hours. The mixture was then cooled and filtered and the mother liquor was evaporated under vacuum. The residue was heated under high vacuum to remove the excess 4-bromobutyronitrile and the residual viscous oil was purified by flash chromatography to give 17.80 g (84% yield).

$^1$H NMR δ(DMSO): 7.83 (s, 4H, Ph), 7.28–7.05 (m, 4H, Ph), 4.46 (t, 1H, Cl-H), 3.67 (m, 1H, C3-H), 3.47 (m, 1H, C3-H'), 2.75 (m, 2H), 2.60–2.30 (m, 6H), 2.05 (m, 1H), 1.95–1.60 (m, 5H) ppm.

Preparation of (XX)

A mixture of XIX (17.45 g, 0.045 mol), 55% hydrazine hydrate (4.25 g, 0.073 mol, 60% excess) and absolute ethanol (550 mL) was stirred and heated at reflux under nitrogen for 4 hours. On cooling a white solid precipitated; it was filtered and washed with cold ethanol (3×75 mL). The combined filtrate was evaporated under vacuum to give a crude yellow solid. This crude solid was dissolved in a mixture of saturated brine (200 mL) and hot ethyl acetate (300 mL) and the layers were separated. The aqueous layer was reextracted with ethyl acetate (3×100 mL). The combined organic layer was dried ($Na_2SO_4$) and solvent was removed at reduced pressure to give 10.8 g of a yellow oil. The crude product was purified by flash chromatography to give 7.65 g (66% yield) of a yellow oil.

$^1$H NMR δ(DMSO): 7.30–7.10 (m, 4H, Ph), 4.45 (t, 1H, Cl-H), 2.95–2.65 (m, 2H), 2.60–2.30 (m, 8H), 2.05 (m, 1H), 1.86 (m, 1H), 1.70 (m, 2H), 1.50 (m, 2H) ppm MS: 259 (NH$^+$, 100)

Preparation of (XXI)

A solution of XX (7.65 g, 0.030 mol) and di-tert-butyl dicarbonate (9.80 g, 0.045 mol) in methylene chloride (400 mL) was stirred at 20° C. under nitrogen for 8 hours. The reaction mixture was then washed with 5% aqueous NaOH solution (150 mL) and the layers were separated. The aqueous layer was reextracted with methylene chloride (3×75 mL) and the combined layer was dried and evaporated to 14.5 grams of a yellow oil. The crude product was purified by flash chromatography to give 10.15 g (95% yield) of a yellow oil.

Preparation of (XXII)

To a suspension of LAH (19.35 g, 0.51 mol) in anhydrous ether (730 mL) was added IV (10.0 g, 0.028 mol) dissolved in anhyrdrous ether (230 mL). The addition was carried out at 0°–5° C. with stirring under a nitrogen atmosphere. After the addition was complete, the suspension was stirred at 5° C. for an additional 30 minutes and then it was stirred at 25° C. under nitrogen for 3 hours. The mixture was now cooled tb 5° C. and the excess LAH was decomposed by the addition of water (110 mL), 10% sodium hydroxide solution (320 mL) and more water (75 mL). Ethyl acetate (365 mL) was then added to the stirred mixture and it was filtered through a celite pad. The pad was washed with ethyl acetate (3×150 mL) and the layers were separated. The aqueous layer was reextracted with ethyl acetate (150 mL). The combined ethyl acetate layer was dried ($Na_2SO_4$) and solvent was removed under vacuum to give 9.27 g (92% yield) of a viscous yellow oil.

Preparation of (XXIII)

A mixture of XXII (7.9 g, 0.022 mol), potassium carbonate (3.03 g, 0.022 mol), N-(3-Bromopropyl)-phthalimide (5.89 g, 0.022 mol) and acetonitrile (175 mL) was stirred and heated at 55°–60° C. under nitrogen for 7 hours. The mixture was then cooled and filtered under vacuum. The mother liquor was evaporated at reduced pressure to give 12.3 g of a viscous oil which was purified by flash chromatography to give 3.3 g (28% yield) of a white solid.

Preparation of (XXIV)

A mixture of XXIII (3.0 g, 5.47 mmol), 55% hydrazine hydrate (0.51 g, 8.77 mmol, 60% excess) and absolute ethanol (120 mL) was stirred and heated at reflux under nitrogen for 5 hours. It was then evaporated under vacuum to give a white solid which was dissolved in a mixture of saturated brine (70 mL) and hot ethyl acetate (100 mL). The layers were separated and the aqueous layer was reextracted with ethyl acetate (2×70 mL). The combined organic layer was dried ($Na_2SO_4$) and solvent was removed at reduced pressure to yield 2.25g (98% yield) of a viscous yellow semi-solid.

Preparation of (XXV)

A solution of XXIV (2.25 g, 5.38 mmol) and di-tert-butyl dicarbonate (4.46 g, 20.4 mmol) in methylene chloride (75 mL) was stirred at 25° C. under nitrogen for 22 hours. The reaction mixture was then washed with 5% aqueous NaOH solution (100 mL) and the layers were separated. The aqueous layer was reextracted with methylene chloride (3×40 mL) and the combined organic layer was dried ($Na_2SO_4$). Removal of solvent at reduced pressure gave 5.65 grams of a yellow oil which was purified by flash column chromatography to give 3.26 g (98% yield) of a yellow oil.

Preparation of 3069

Ether saturated with HCl gas (30 mL) was added to a solution of XXV (3.16 g, 5.22 mmol) dissolved in methanol (60 mL). The solution was stirred at 25° C. for 3½ hours. Solvents were removed under vacuum to give 2.29 g of an off-white solid which was purified by heating it in water (300 mL) containing Norit (480 mg) at 90°–95° C. for 5 minutes. The mixture was filtered hot through a celite pad and the pad was washed with hot water (3×150 mL). The colorless filtrate was evaporated under vacuum at 60° C. Hexane was added to the residue and solvent was removed under vacuum. Finally, methanol (100 mL) was added to the residue. Its removal under reduced pressure gave 2.16 g (91%) of a hygroscopic white solid.

Anal. calcd for C$_{19}$H$_{38}$Cl$_4$N$_4$.H$_2$O: C, 47.31; H, 8.36; Cl, 29.40; N, 11.62 Found: C, 47.71; H, 8.21; Cl, 29.25; N, 11.65

$^1$H NMR δ(DMSO): 7.62 (d, 1H, Ph), 7.58–7.40 (m,3H, Ph), 5.28 (dd, 1H, C1-H),3.30–3.0 (m, 14H,), 2.58 (m, 1H, C2-H'), 2.40 (m, 1H, C2-H), 2.30–2.05 (m, 4H), 2.0–1.6 (m, 4H) ppm MS: 319 (MH$^+$) HPLC: 99%

Example 8:

Preparation of II

A mixture of N,N-Bis-4-aminobutyl racemic aminoindan (compound no. 2711, 2.5g, 6.5mmol), N,N-di-tert-butoxycarbonylthiourea, (Iwanowicz E et al. Synthetic Communications (1993) 23, 1443), (3.5 g, 13.0 mmol), triethyl amine (3.61 g, 35.75 mmol) and dry DMF (19.5 mL) was stirred at 0° C. under nitrogen for an hour. The ice bath was removed and the mixture was then stirred at 22°–24° C. under nitrogen for 22 hours. Ethyl acetate (200 mL) was added and the mixture was filtered through a Celite pad. The pad was washed with ethyl acetate (4×70 mL). The combined filtrates were washed with water (200 mL), sat. sodium chloride (200 mL) and dried (Na$_2$SO$_4$). Removal of solvent gave 6.2 g of a viscous semi-solid. The crude product was purified by flash chromatography using hexane/ethyl acetate 70/30 as etuent. This gave 3.5 g 71% yield) of an off-white hygroscopic solid.

Preparation of III

A mixture of N-4-aminobutyl racemic aminoindan (2710, 3.33g, 12.0 mmol), N,N-di-tert-butoxycarbonylthiourea, (Iwanowicz E et al. Synthetic Communications (1993) 23, 1443), (3.32 g, 12.0 mmol), triethylamine (4.85 g, 48.0 mmol) and dry DMF (30 mL) was treated and worked up according to the conditions used for the preparation of II. Removal of solvent gave 6.0 g of a viscous oil/semi-solid. The crude product was purified by flash chromatography using methylene chloride/methanol 94/6 as eluent. This gave 3.5 g (65.5% yield) of a viscous brown oil.

Preparation of (N,N-di -(4-Guanidinobutyl )-aminoindan-3HCl (3042)

To a solution of II (3.0 g, 3.95 mmol) dissolved in ether (10 mL) was added ether saturated with HCl gas (10 mL). A gummy oil precipitated. Then methanol (40 mL) was added and the solution was stirred at 25° C. for 30 minutes. Solvents were removed under vacuum to give 3.2 g of a white solid. It was purified by heating it in water (150 mL) containing Norit (500 mg) at 90°–95° C. for 5 minutes. The mixture was filtered hot through a Celite pad and the pad was washed with hot water (2×100 mL). The colorless filtrate was evaporated under vacuum at 60° C. Hexane was added to the residue and solvent was removed under vacuum. Finally, methanol (100 mL) was added to the residue. Its removal under reduced pressure gave a white solid (1.60 g, 86%) which was dried at 40° C. under high vacuum and stored in a desiccator over phosphorus pentoxide.

Anal. for C$_{19}$H$_{36}$C$_{13}$N$_7$2H$_2$O: C,45.2;H,7.98,N,19.42 Found: C,44.90,H,6.65;N,19.06 $^1$H NMR δ(D$_2$O): 7.60–7.30 (m, 4H, Ph) ,5.20 (dd, 1H, C1-H) 3.40–3.0 (m,9H),2.90(M,1H,C3-H),2.52(m, 1H,C2-H), 2.36 (m, 1H, C2-H'''), 2.0–1.4 (m, 8H) ppm.

FABMS: 360 (MH$^+$), 396 (MH$^+$+HCl).
IR(KBr) :3397,1665,1464,1167,766cm$^{-1}$.
HPLC: 96%

Preparation of (N-(4-Guanidinobutyl)-aminoindan.2HCl) (3043)

Ether saturated with HCl gas (15 mL) was added to a solution of III (305 g, 7.85 mmol) dissolved in ether (10 mL). A gummy solid precipitated. Then methanol (50 mL) was added and the solution was stirred at 25° C. for 30 minutes. Solvents were removed under vacuum to give 3.3 g of a white solid, which was purified by heating in water (180 mL) containing Norit (560 mg) at 90°–95° C. for 5 minutes. The mixture was filtered hot through a Celite pad and the pad was washed with hot water (2×100 mL). The colorless filtrate was evaporated under vacuum at 60° C. Hexane was added to the residue and solvent was removed under vacuum. Finally, methanol (100 mL) was added to the residue. Its removal under reduced pressure gave 2.14 g (86%) of an extremely hygroscopic white solid which was dried at 25° C. under high vacuum and stored in a desiccator over P$_2$O$_5$.

Anal. calcd. for C$_{14}$H$_{24}$Cl$_2$N$_4$.H$_2$O: C,49.85;H,7.77;N, 16.6 Found: C,49.11;H,7.63;N,16.70

$^1$H NMR δ(D$_2$O): 7.60–7.30(m,4H,Ph) ,4.8(m, 1H,C1-H) ,3.30–3.05 (m, 5H), 3.0 (m, 1H, C3 -H), 2.55 (m, 1H, C2-H), 2.26 (m, 1H,C2-H) 1.80–160 (m,4H)ppm FABMS: 247 (MH$^+$), 283 (MH$^+$+HCl). IR (KBr): 3349, 3161,2950,2803,1665,1462,1169,765cm$^{-1}$. HPLC: 95%

STRUCTURES OF COMPOUNDS

2709

2710

2711

2726 (R)-2711

2727 (S)-2711

2722

2728

2720

2724

-continued
STRUCTURES OF COMPOUNDS

Names of Some Compounds

| Compound Number | Compound Name |
| --- | --- |
| 2709 | N-(3-aminopropyl)-1-aminoindan |
| 2710 | N-(4-aminopropyl)-1-aminoindan |
| 2711 | racemic N,N-di(4-amino-n-butyl)-1-aminoindan |
| 2726 | (R)-N,N-di(4-amino-n-butyl)-1-aminoindan |
| 2727 | (S)-N,N-di(4-amino-n-butyl)-1-aminoindan |
| 2722 | N-(4-amino-n-butyl)-N-(3-amino-n-propyl)-1-aminoindan |
| 2728 | N,N-di(4-amino-n-butyl)-1-amino-1,2,3,4-tetrahydronaphthalene |
| 2720 | N-[N-(4-aminobutyl)-3-aminopropyl)]-1-aminoindan or N-(1-indanyl)-N'-(4-aminobutyl)-1,3-diaminopropane |
| 2724 | N-[N-(3-aminopropyl)-4-aminobutyl)]-1-aminoindan or N-(1-indanyl)-N'-(3-aminopropyl)-1,4-diaminobutane |
| 2721 | N-{[N-(3-aminopropyl)-4-aminobutyl)]-N'-3-aminopropyl}-1-aminoindan or N-(1-indanyl)-N'-[N-(3-aminopropyl)-4-aminobutyl]-1,3-diaminopropane |
| 2725 | N-{[N-(4-aminobutyl)-3-aminopropyl)]-N'-4-aminobutyl}-1-aminoindan or N-(1-indanyl)-N'-[N-(4-aminobutyl)-3-aminopropyl]-1,4-diaminobutane |
| 2717 | cis N,N'-diacetyl-1,3-diaminoindan |
| 2718 | trans N,N'-diacetyl-1,3-diaminoindan |
| 2715 | cis 1,3-diaminoindan |
| 2716 | trans 1,3-diaminoindan |
| 2731 | N-(4-aminobutyl)-1,3-diaminoindan |
| 2732 | N,N'-di(4-aminobutyl)-1,3-diaminoindan |
| 3069 | N-(3-aminopropyl)-N-[N-(3-aminopropyl)-4-aminobutyl]-1-aminoindan |
| 3042 | N,N-di(4-guanidinobutyl)-1-aminoindan |
| 3043 | N-(4-guanidinobutyl)-1-aminoindan |

BIOLOGICAL EXAMPLES

1. Cultures of Dissociated Neonatal Rat Cerebellum

A. Reversal of NMDA Induced Cell Death

The cerebellum was aseptically dissociated from 6 or 7-day old rat pups and placed in a 15 ml sterile plastic conical tube containing 3 ml of Dulbecco's modified Eagle's medium (DMEM) with a high glucose concentration (1 g/ml) and 2 mM (v/v) L-glutamine and an antibiotic anti-mitotic mixture. The cerebella were then dissociated after 20–25 passages through a sterile 13 gauge, 10 cm long stainless steel needle attached to a 5 ml syringe with an inserted 45 micrometer pore nylon sieve. The dissociated cells were centrifuged at 200 g for 5 minutes. The supernatant was discarded and the cells resuspended in medium enriched with 15% (v/v) heat inactivated fetal calf serum. Cell viability was determined by the tryptan blue exclusion test.

Cells were plated at a density of 200/mm² on poly-L-lysine coated surfaces. Poly-L-lysine coated glass coverslips were prepared at least one hour in advance of plating by immersing sterile coverslips in sterile distilled water solution containing 15 microgram/ml poly-L-lysine, and washing in sterile water just prior. to use. The plated cells were covered with enriched medium and incubated at 37° C. in an atmosphere of 5% $CO_2$ in air and 97% humidity. After three days in culture, the media was replaced with media containing the desired test compound. Each test compound was tested in duplicate. Toxic-dose response was determined for each compound over a range from 0.005–1000 micromole. Four groups were run in each set of experiments;

I. Control, consisting of enriched media alone,

II. N-methyl-D-aspartate (NMDA, 1 mM for 3 hours) as the cytotoxic challenge,
III. Test compound plus NMDA, and
IV. Positive control, spermine, spermidine or putrescine (0.01 micromoles) plus NMDA.

Nerve cell survival was evaluated by phase contrast microscopy and tryptan blue staining after 24 hours.

Results

The results are shown in Table 1 below. Surviving cells in Culture are measured relative to control (100%) as described above. Percent protection is the Cell Survival for the test compound minus the NMDA effect. Thus, maximal protection is 100% minus 30% NMDA effect i.e. 70%. The Effective Protection was calculated as the percent of the Percent Protection (X) divided by the maximal protection value (e.g. X×100/70).

TABLE 1

| COMPOUND | EXPERMNT'L GROUP Dose (μM) | SURVIVING CELL IN CULTURE | PERCENT PROTECTION | EFFECTIVE PROTECTION |
| --- | --- | --- | --- | --- |
| | Control | 100 | | |
| | NMDA | 30 | | |
| | Max protection | | 70 | 100 |
| | Spermine + NMDA | 68 | 38 | 54 |
| | Spermidine + NMDA | 78 | 48 | 69 |
| Putrescine | 30 + NMDA | 0 | 0 | |
| (R)-1-aminoindan | 0.005 | 80 | 50 | 71 |
| | 0.010 | 30 | 0 | 0 |
| | 0.100 | 28 | −2 | — |
| 2709 | 0.005 | 26 | −4 | — |
| | 0.010 | 53 | 23 | 33 |
| | 0.100 | 59 | 29 | 41 |
| | 1.000 | 43 | 13 | 18* |
| | 10.00 | 38 | 8 | 11 |
| 2710 | 0.100 | 72 | 42 | 60 |
| | 1.000 | 70 | 40 | 57 |
| 2711 | 0.005 | 74 | 44 | 63 |
| | 0.010 | 68 | 38 | 54 |
| | 0.100 | 62 | 32 | 46 |
| 2715 | 0.005 | 49 | 19 | 27 |
| | 0.100 | 42 | 12 | 17 |
| | 1.000 | 32 | 2 | 3 |
| 2716 | 0.005 | 65 | 35 | 50 |
| | 0.010 | 30 | 0 | 0 |
| | 0.100 | 25 | −5 | — |
| | 1.000 | 30 | 0 | 0 |
| 2720 | 0.005 | 72 | 42 | 60 |
| | 0.010 | 38 | 8 | 11 |
| | 0.100 | 32 | 2 | 3 |
| 2721 | 0.005 | 28 | −2 | — |
| | 0.010 | 26 | −4 | — |
| 2722 | 0.005 | 115 | 85 | 121 |
| | 0.010 | 87 | 57 | 81 |
| 2724 | 0.005 | 95 | 65 | 93 |
| | 0.010 | 87 | 57 | 81 |
| 2725 | 0.005 | 72 | 42 | 60 |
| | 0.010 | 38 | 8 | 11 |
| | 0.100 | 32 | 2 | 3 |
| 2728 | 0.005 | 20 | −10 | — |
| | 0.010 | 86 | 56 | 80 |
| 2726 | 0.005 | 129 | 99 | 141 |
| | 0.010 | 55 | 25 | 36 |
| 2727 | 0.005 | 30 | 0 | 0 |
| | 0.010 | 55 | 25 | 36 |

TABLE 2

| COMPOUND | TOXICITY $TD_{50}$ μM |
| --- | --- |
| Spermine | 2 |
| Spermidine | 2 |
| Putrescine | 300 |
| (R)-1-aminoindan | 175 |
| 2709 | 50 |
| 2710 | 30 |
| 2711 | 60 |
| 2715 | 10 |
| 2716 | 0.7 |
| 2720 | 0.2 |
| 2721 | 1 |
| 2722 | 20 |

B: In Vitro Cell Toxicity

Toxic dose-response curves were compiled using the protocol described above. The TD50 values calculated appear in Table 2 below.

TABLE 2-continued

| COMPOUND | TOXICITY TD$_{50}$ μM |
|---|---|
| 2724 | 4 |
| 2725 | 20 |
| 2728 | 0.25 |
| 2726 | 1.7 |
| 2727 | 0.4 |

2. Global Brain Ischemia In Gerbils

Male mongolian gerbils, aged 2.5–5 months, housed 4–8 in a cage, were supplied freely with food and water and maintained at 24° C. with a 12 hour day/night cycle.

For surgery the animals were anesthetized with halothane (1.5% in 100% $O_2$) and the common carotid arteries exposed bilaterally through a midline ventral neck incision. Each artery was clamped for 5 minutes with aneurysm clips to produce global brain ischemia. The anesthesia was discontinued upon clamping. After 5 minutes the clamps were removed and the wound closed with skin clips.

For treatment, the test compound or vehicle was injected intra-peritoneally (ip) in a volume of 50 microlitres of solvent per 10 g body weight. The first injection was given two minutes after clamp removal, and thereafter daily for the next 2 post-operative days (total of 3 injections).

Seven groups each of 4–8 animals were compared:
I. Control; (sham- or unoperated and saline treated),
II. Vehicle treated, unoperated (when solvent is other than saline),
III. Ischemia—untreated or saline treated),
IV. Ischemia—vehicle treated (when solvent is other than saline),
V. Ischemia—Test compound treated, one sub-group per concentration tested,
VI. Ischemia and pentobarbital (40 mg/kg) as positive control).

Analysis of neuronal damage was performed 14 days post-ischemia by counting pyramidal neurons throughout the CA1 layer of the anterior hippocampus in 4 micromolar thick (paraffin) coronal brain sections stained with hematoxylin and erosin.

The Results are shown in the Table 3 below. Percent Protection values represent the fraction of hippocampi protected from ischemia in a group of animals treated with the stated dose of compound.

TABLE 3

| TEST COMPOUND (n) | DOSE (mg/kg) | % INTACT NEURONS | PERCENT PROTECTION |
|---|---|---|---|
| TO ADD ACTIVITY OF POLYAMINES | | | |
| Control | | 100 | |
| Ischemia | | 0 | |
| Pentobarbital (8) | | | 87.5 |
| Spermine | 10.0 | | 60 |
| Spermidine | 10.0 | | 42 |
| Putrescine | 10.0 | | 41 |
| (R)-1-aminoindan | | | |
| (4) | 0.1 | | 25.0 |
| (4) | 1.0 | | 25.0 |
| (4) | 10.0 | | 25.0 |
| (S)-1-aminoindan | | | |
| (4) | 0.1 | | 0 |
| (4) | 1.0 | | 50.0 |
| (4) | 10.0 | | 75.0 |
| 2709 | | | |
| (4) | 1.0 | | 12 |
| (8) | 10.0 | | 31 |
| 2710 | | | |
| (4) | 1.0 | | 25 |
| (8) | 10.0 | | 37 |
| 2711 | | | |
| (4) | 1.0 | | 50 |
| (12) | 10.0 | | 86 |
| (5) | 10.0 | | 70 |
| 2715 | | | |
| (4) | 1.0 | | 75 |
| (7) | 10.0 | | 50 |
| 2716 | | | |
| (4) | 1.0 | | 50 |
| (7) | 10.0 | | 0 |
| 2720 | | | |
| (2) | 1.0 | | — |
| (12) | 10.0 | | 58 |
| 2721 | | | |
| (8) | 1.0 | | 12 |
| (6) | 10.0 | | 67 |
| 2722 | | | |
| (4) | 1.0 | | 50 |
| (4) | 10.0 | | 25 |
| 2724 | | | |
| (4) | 1.0 | | 12 |
| (13) | 10.0 | | 56 |
| 2725 | | | |
| (4) | 1.0 | | 0 |
| (4) | 10.0 | | 25 |
| 2728 | | | |
| (5) | 1.0 | | 20 |
| (5) | 10.0 | | 80 |
| (5) | 10.0 | | 40 |
| 2726 (4) | 10.0 | | 50 |
| 2727 (7) | 10.0 | | 28.5 |

What is claimed is:

1. A compound of the formula:

wherein n is 1 or 2;

$R_1$ and $R_2$ are each independently hydrogen, hydroxy, substituted or unsubstituted $C_{1-4}$ alkyl, substituted or unsubstituted $C_{1-4}$ alkoxy or halogeno;

$R_5$ is hydrogen, substituted or unsubstituted $C_{1-4}$ alkyl or $NR_6R_7$;

$R_3$, $R_4$, $R_6$ and $R_7$ are each independently hydrogen or $(CH_2)_m$—[NH(CH_2)_x]_y—NHR_{11}$ wherein m is from 1–5, y is from 0–5 and each x is independently from 1–5 and $R_{11}$ is hydrogen or $C(NH)NH_2$;

provided that when $R_3$ and $R_4$ are both hydrogen, $R_5$ is $NR_6R_7$;

pharmaceutically acceptable salts and optically active isomers thereof.

2. The compound of claim 1, wherein n is 1.

3. The compound of claim 1, wherein $R_1$, $R_2$ and $R_5$ are hydrogen.

4. The compound of claim 1, wherein $R_3$ is $(CH_2)_m$—[NH(CH_2)_x]_y—NHR_{11}$ and $R_4$ is hydrogen.

5. The compound of claim 4, wherein $R_{11}$ is hydrogen.

6. The compound of claim 4, wherein m is 3 or 4.

7. The compound of claim 4, wherein y is 0, 1 or 2.

8. The compound of claim 4, wherein each x is 3 or 4.

9. The compound of claim 4, wherein y is greater than 1, and each x is 3 or 4.

10. The compound of claim 4, wherein $R_{11}$ is $C(NH)NH_2$.

11. The compound of claim 1, wherein both $R_3$ and $R_4$ are $(CH_2)_m$—[NH(CH_2)_x]_y—NHR_{11}$.

12. The compound of claim 11, wherein $R_{11}$ is hydrogen.

13. The compound of claim 11, wherein m is 3 or 4.

14. The compound of claim 11, wherein y is 0, 1 or 2.

15. The compound of claim 14, wherein y is 0.

16. The compound of claim 11, wherein $R_{11}$ is $C(NH)NH_2$.

17. The compound of claim 1, wherein $R_3$ and $R_4$ are hydrogen; and $R_5$ is $NR_6R_7$.

18. The compound of claim 17, wherein m is 3 or 4; y is 0, 1 or 2; and each x is 3 or 4.

19. The compound of claim 17, wherein $R_5$ is $NR_6R_7$.

20. The compound of claim 19, wherein $R_6$ is hydrogen; and $R_7$ is $(CH_2)_m$—[NH(CH_2)_x]_y—NHR_{11}$.

21. The compound of claim 20, wherein m is 3 or 4; y is 0; and $R_{11}$ is hydrogen.

22. The compound of claim 1, wherein $R_5$ is trans with respect to $NR_3R_4$.

23. The compound of claim 1, wherein $R_5$ is cis with respect to $NR_3R_4$.

24. The compound of claim 1, wherein the ring carbon to which $NR_3R_4$ is bound is in the R configuration.

25. The compound of claim 1, wherein the ring carbon to which $NR_3R_4$ is bound is in the S configuration.

26. The compound of claim 1, selected from the group consisting of:

N-(3-aminopropyl)-1-aminoindan;

N-(4-aminopropyl)-1-aminoindan;

N,N-di(4-amino-n-butyl)-1-aminoindan;

(R)-N,N-di(4-amino-n-butyl)-1-aminoindan;

(S)-N,N-di(4-amino-n-butyl)-1-aminoindan;

N-(4-amino-n-butyl)-N-(3-amino-n-propyl)-1-aminoindan;

N,N-di(4-amino-n-butyl)-1-amino-1,2,3,4-tetrahydronaphthalene;

N-[N-(4-aminobutyl)-3-aminopropyl)]-1-aminoindan;

N-[N-(3-aminopropyl)-4-aminobutyl)]-1-aminoindan;

N-{([N-(3-aminopropyl)-4-aminobutyl)]-N,-3-aminopropyl}-1-aminoindan;

N-{[N-(4-aminobutyl)-3-aminopropyl)]-N,-4-aminobutyl}-1-aminoindan;

cis 1,3-diaminoindan;

trans 1,3-diaminoindan;

N-(4-aminobutyl)-1,3-diaminoindan;

N,N'-di(4-aminobutyl)-1,3-diaminoindan;

N-(3-aminopropyl)-N-[N-(3-aminopropyl)-4-aminobutyl]-1-aminoindan;

N,N-di(4-guanidinobutyl)-1-aminoindan;

N-(4-guanidinobutyl)-1-aminoindan, or a pharmaceutically acceptable salt thereof.

27. A pharmaceutical composition comprising a therapeutically effective amount of the compound of claim 1 and a pharmaceutically acceptable carrier.

28. The pharmaceutical composition of claim 27, wherein the pharmaceutically acceptable carrier is a solid and the pharmaceutical composition is a tablet.

29. The pharmaceutical composition of claim 27, wherein the therapeutically effective amount is from about 1 mg to about 1000 mg.

30. The pharmaceutical composition of claim 29, wherein the therapeutically effective amount is from about 10 mg to about 100 mg.

31. The pharmaceutical composition of claim 27, wherein the pharmaceutically acceptable carrier is a liquid and the pharmaceutical composition is an injectable solution.

32. The pharmaceutical composition of claim 31, wherein the therapeutically effective amount is from about 1 mg/ml to about 1000 mg/ml.

33. The pharmaceutical composition of claim 32, wherein the therapeutically effective amount is from about 10 mg/ml to about 100 mg/ml.

34. The pharmaceutical composition of claim 27, wherein the carrier is a gel and the pharmaceutical composition is a suppository.

35. A method of treating acute neurological traumatic disorder or neurotrauma in a subject comprising administering to the subject a therapeutically effective amount of the compound of claim 1 or pharmaceutically acceptable salt thereof, effective to treat the acute neurological traumatic disorder or neurotrauma in the subject.

36. A method of treating a subject afflicted with a neurodegenerative disease which comprises administering to the subject an amount of the compound of claim 1 or pharmaceutically acceptable salt thereof, effective to treat the neurodegenerative disease in the subject.

37. A method of treating a subject afflicted with a neurotoxic injury which comprises administering to the subject an amount of the compound of claim 1 or pharmaceutically acceptable salt thereof, effective to treat the neurotoxic injury in the subject.

38. A method of treating a subject afflicted with brain ischemia which comprises administering to the subject an amount of the compound of claim 1 or pharmaceutically acceptable salt thereof, effective to treat brain ischemia in the subject.

39. A method of treating a subject afflicted with a head trauma injury which comprises administering to the subject an amount of the compound of claim 1 or pharmaceutically acceptable salt thereof, effective to treat the head trauma injury in the subject.

40. A method of treating a subject afflicted with a spinal trauma injury which comprises administering to the subject an amount of the compound of claim 1 or pharmaceutically acceptable salt thereof, effective to treat the spinal trauma injury in the subject.

41. A method of preventing nerve damage in a subject which comprises administering to the subject an amount of the compound of claim 1 or pharmaceutically acceptable salt thereof, effective to prevent nerve damage in the subject.

* * * * *